United States Patent [19]

Loretz

[11] 4,357,105

[45] Nov. 2, 1982

[54] BLOOD DIAGNOSTIC SPECTROPHOTOMETER

[75] Inventor: Thomas J. Loretz, Sturbridge, Mass.

[73] Assignee: Buffalo Medical Specialties Mfg., Inc., St. Petersburg, Fla.

[21] Appl. No.: 173,801

[22] Filed: Aug. 6, 1980

[51] Int. Cl.³ .................... G01N 21/25; G01N 21/35; G01N 33/48

[52] U.S. Cl. ...................... 356/40; 356/41; 356/73; 356/414

[58] Field of Search .................... 356/39–42, 356/414, 420, 73; 250/226; 362/800; 350/316

[56] References Cited

U.S. PATENT DOCUMENTS

| | | |
|---|---|---|
| 2,486,956 | 11/1949 | Lundberg . |
| 3,437,822 | 4/1969 | Fitzsimmons . |
| 3,533,698 | 10/1970 | Brown et al. ......................... 356/40 |
| 3,647,299 | 3/1972 | Lavallee ............................. 250/226 |
| 3,704,950 | 12/1972 | Rosencranz . |
| 3,706,499 | 12/1972 | Rapoza et al. . |
| 3,709,615 | 1/1973 | Blakeslee . |
| 3,736,427 | 5/1973 | Allington ............................ 250/461 |
| 3,743,429 | 7/1973 | Kawai ................................. 356/414 |
| 3,752,995 | 8/1973 | Liedholz . |
| 3,755,679 | 8/1973 | Otsuka ................................ 307/311 |
| 3,833,864 | 9/1974 | Kiess et al. . |
| 3,883,250 | 5/1975 | Unuma et al. ...................... 350/316 |
| 3,902,812 | 9/1975 | Honkawa . |
| 3,910,701 | 10/1975 | Henderson et al. . |
| 3,921,066 | 11/1975 | Angel et al. . |
| 3,922,088 | 11/1975 | Lübbers et al. ..................... 356/419 |
| 3,952,206 | 4/1976 | Liedholz . |
| 3,977,011 | 8/1976 | Matsuda . |
| 3,992,113 | 11/1976 | Egli et al. . |
| 3,994,585 | 11/1976 | Frey .................................... 356/40 |
| 4,228,349 | 10/1980 | Ettenberg et al. ................. 250/226 |

Primary Examiner—William H. Punter
Attorney, Agent, or Firm—Hosier, Niro & Daleiden, Ltd.

[57] ABSTRACT

A compact, portable, clinical instrument dedicated to hemoglobin determination employs an L.E.D. light source with a peak output wavelength of about 553 nanometers and a yellow-blocking filter with a long wavelength cut-off not longer than about 565 nanometers. Thus, the relative amount of energy incident upon the blood sample in the 540 nm. hemoglobin absorption band is maximized. In addition to the L.E.D., the photodetector and the amplifying, inverting, log conversion, digital conversion, display and power supply regulation circuits are also exclusively solid-state. The display is of the reflective or liquid crystal type, and the power supply regulator is a sophisticated integrated circuit containing the equivalent of many discrete components. As a result, current consumption is minimized, and battery life and instrument accuracy are maximized. As an alternative illumination source, an infra-red L.E.D. can be employed, and the instrument is then capable of blood turbidity measurement. In either case, the L.E.D. illumination source is powered by a constant-current regulator, which minimizes errors due to fluctuations in illumination intensity.

6 Claims, 4 Drawing Figures

BLOOD DIAGNOSTIC SPECTROPHOTOMETER

This invention relates generally to spectrophotometric instruments. It particularly concerns a portable clinical heomglobinometer and blood turbidity instrument.

BACKGROUND

Hemoglobin measurement is recognized as one of the most useful procedures in clinical medicine, particularly for the detection of anemia. But such measurements have not generally been carried out with a high degree of accuracy. General purpose laboratory spectrophotometers are accurate, but they are unsuitable for general clinical use because they are expensive and require elaborate set-up procedures. Other photometers are available which are dedicated exclusively to hemoglobin determination. These are relatively inexpensive and easy to use, and are often employed in clinical settings such as doctor's offices and hospitals. For maximum convenience such instruments are usually small, portable and battery-powered. But these clinical instruments are not as accurate as might be desired.

Blood turbidity is another measurement which has diagnostic significance. Such measurements can also benefit from an improvement in the accuracy of clinical instruments.

There are a lot of separate factors, each of which makes some partial contribution of its own to the inaccuracy of such instruments. The batteries (power cells) which supply power for portable instruments tend to change their output over time, as they become exhausted; and this causes changes in the intensity of the illumination, which is an important source of inaccuracy. Any reduction in current drain therefore contributes to accuracy by extending battery life. Use of solid-state circuitry exclusively is one way to reduce current drain. Light-emitting diodes (L.E.D.'s), for example, consume less current than incandescent light sources. Solid state photodetectors are also superior in this respect to photomultipliers and other vacuum tube devices. Even within the field of solid-state circuitry, some devices require less power than others; thus a reflective (liquid crystal) type of digital display device is preferable to a galvanometer read-out or even to a digital display of the L.E.D. type.

It is also important to regulate battery output as closely as possible in order to minimize inaccuracies due to supply changes. A single Zener diode cannot do as good a job as a sophisticated integrated circuit regulator which contains the equivalent of many discrete components.

Spectral purity is a major determinant of spectrophotometric accuracy where hemoglobin determinations are concerned. Such determinations are commonly based on absorbance of green light at a wavelength of 540 nanometers, which obeys the Beer-Lambert law. When the illumination employed contains other spectral components, this law becomes a less accurate description of the absorbance function, and an instrument based on it is subject to some degree of inherent inaccuracy. In the past the light sources used in clinical hemoglobinometers have had spectral characteristics spanning the green-yellow range, and yellow-blocking filters have been used to discard the undesired yellow portion of the output. As a result, the usable light output has been severely reduced, and the signal-to-noise ratio adversely affected. It is desirable that the peak output of the unfiltered light source approached as closely as possible to the 540 nm. wavelength of interest. Furthermore, if the light source has a significant output in other regions of the spectrum, it is desirable that filters be used which cut off transmission as close as possible to the desired wavelength.

SUMMARY OF THE INVENTION

According to one aspect of this invention, a hemoglobinometer is designed to operate with illumination as close as possible to a wavelength of 540 nm., but with as little sacrifice of intensity as possible. Thus, a hemoglobinometer is provided which comprises a light source having an unfiltered peak output wavelength not longer than about 553 nm., and filter means having a long wavelength transmission cut-off not longer than about 565 nm.

According to another aspect of this invention, each source of inaccuracy is reduced simultaneously to the lowest practicable level, while still retaining all those features of compactness, portability and low cost which are considered important in a clinical instrument. Thus a portable hemoglobinometer is provided which comprises means for receiving at least one power cell, solid-state means for regulating the output of the power cell, a solid-state light source connected to be powered by the regulated output, a solid-state photodetector, solid-state means for inverting and logarithmically converting the light-measurement signal from the photodetector, solid-state means for digital conversion of the inverted and logarithmically converted signal, and reflective solid-state digital display means connected to display the results of the digital conversion.

Preferably the regulator is not merely a single Zener diode, but a sophisticated integrated circuit, i.e. one which contains the equivalent of a plurality of discrete diode and transistor components.

Preferably these current-saving design features are combined in one instrument with the appropriate choice of light source and filter characteristic to operate with a high intensity of illumination and as close as practicable to 540 nm., while at the same time keeping the power supply output (and, therefore, the illumination intensity) as constant as possible over the life of the battery.

While the hemoglobinometer of this invention is a dedicated instrument, i.e. one which is designed to perform hemoglobin determinations at a fixed wavelength, it nevertheless has a measure of versatility in that it is capable of using either the oxyhemoglobin or the cyanmethhemoglobin method. For convenience, the instrument is simply switched electrically from either mode to the other. Zero set is also an electrical adjustment. When equipped with an alternate infra-red illumination source, it can also be used to perform blood turbidity measurements with high accuracy.

The features of the invention will be more fully appreciated from the detailed description herein, when read in conjunction with the accompanying drawings.

DRAWINGS

DETAILED DESCRIPTION OF THE PREFERRED EMBODIMENT

Figure 1:
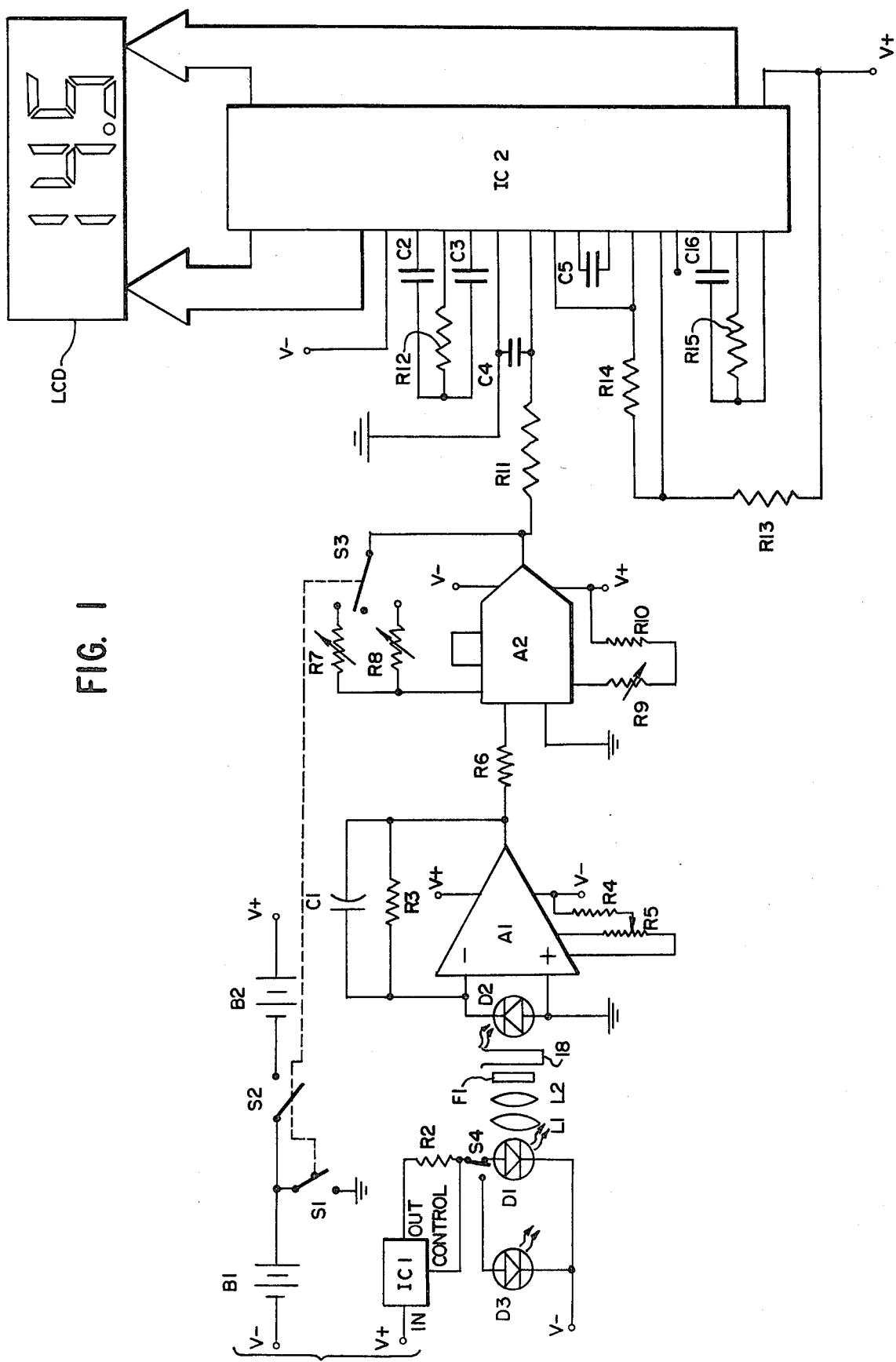
FIG. 1 is a schematic electrical circuit diagram of an instrument in accordance with this invention.

When radiant energy passes through a liquid, certain wavelengths may be selectively absorbed by particles which are dissolved therein. For a given path length which the light traverses through the liquid, Beer's law (the Beer-Lambert or Bouguer-Beer relation) indicates that the relative reduction in radiation power (P/Po) at a given wavelength is an inverse logarithmic function of the concentration of the solute which absorbs that wavelength. For a solution of human hemoglobin, the absorption maximum is at a wavelength of about 540 nanometers. Therefore, measurements of absorption at this wavelength are capable of delivering clinically useful information as to hemoglobin levels in a properly prepared blood sample.

But the application of this long-known principle to the design of a diagnostic instrument, particularly one which is compact, portable and inexpensive, involves overcoming a number of practical problems. First, instead of measuring the reduction in radiation power directly, it is necessary to measure the reduced radiation power level emerging from the blood sample, and then compare that level to the level which is believed to be incident upon the sample. The assumption must be made, therefore, that incident illumination has remained at the expected level during the measurement, i.e. that the light source output is constant.

The light output, however, is dependent in part upon the power supply output. Thus, it is important to stabilize the illumination power supply. This objective, in turn, requires reducing the current drain imposed upon the power supply during operation of the instrument. Batteries (power cells) employed in portable instruments are vulnerable to changes in output as a function of remaining battery life. Therefore, in a portable instrument it is particularly important to slow the process of battery exhaustion by minimizing current drain.

There is another practical problem which must be considered in the design of an instrument for hemoglobin determination. As noted previously, the quantity actually measured is the radiation power level emerging from the sample. But this power level is measured at all wavelengths within the sensitivity range of the detector, whereas in the case of hemoglobin absorption the desired clinical information is contained only in the wave band near 540 nm. Radiation in other spectral regions which emerges from the sample is noise; it causes the detector to overestimate the emerging power level at the wavelength of interest, and, therefore, to underestimate the absorption due to hemoglobin in the solution. This reduces the accuracy of the hemoglobin determination.

Prior art hemoglobinometers have employed light sources with a peak output toward the yellow region of the spectrum (about 565 nm.), for example, undoped gallium arsenide L.E.D.'s. The light output of these devices falls off dramatically at 540 nm. Thus an instrument designed to work at the latter wavelength must operate at greatly reduced signal strength. This, in turn, requires high levels of amplification, with an attendant sacrifice of linearity. Sensitivity (detection threshold) is also adversely affected by such low signal levels.

Referring to FIG. 1 of the drawings, a portable hemoglobinometer in accordance with this invention has a power supply with provision for two power cells B1 and B2 which supply two separate potentials V+ and V−. A pair of ganged switches S1 and S2 turn the power supply on and off.

A voltage regulator IC1 operates in constant current mode, and drives a light source in the form of a light-emitting diode D1. The voltage regulator IC1 is an integrated circuit, such as National Semiconductor's model LM317H or the equivalent. The manufacturer's schematic diagram for the internal circuitry of this chip shows it to have the equivalent of the following discrete components: three separate Zener diodes and twenty-six separate transistors, of which one is a field-effect type; and of the twenty-five bipolar devices, two are of the double emitter or double collector type. This type of voltage regulator maintains a much more constant current to the light source D1 than a conventional regulator of the simple shunt Zener diode type. The brightness of the light output of diode D1 is a function of the diode current rather than its supply voltage. Therefore, the described current regulation approach causes the illumination to be held substantially constant over battery life. In addition, since voltage regulator IC1 is an all-solid-state device, it consumes minimal power, a fact which extends battery life and thus further stabilizes the supply current for the light source D1.

The output current of regulator IC1 develops a feedback voltage across a resistor R2 which is applied as a control signal for the regulator via a line 10. The value of R2 is chosen to provide a regulator output current of approximately 30 ma. which is fed through the light source D1.

Since the light source is an L.E.D., it consumes minimal power by comparison to incandescent light sources, and thus further extends battery life. L.E.D. light sources also have superior light output constancy with age, as compared to incandescent filaments which change their intensity as they are consumed. Constancy of light output is essential to the stability of the instrument.

Figure 2:
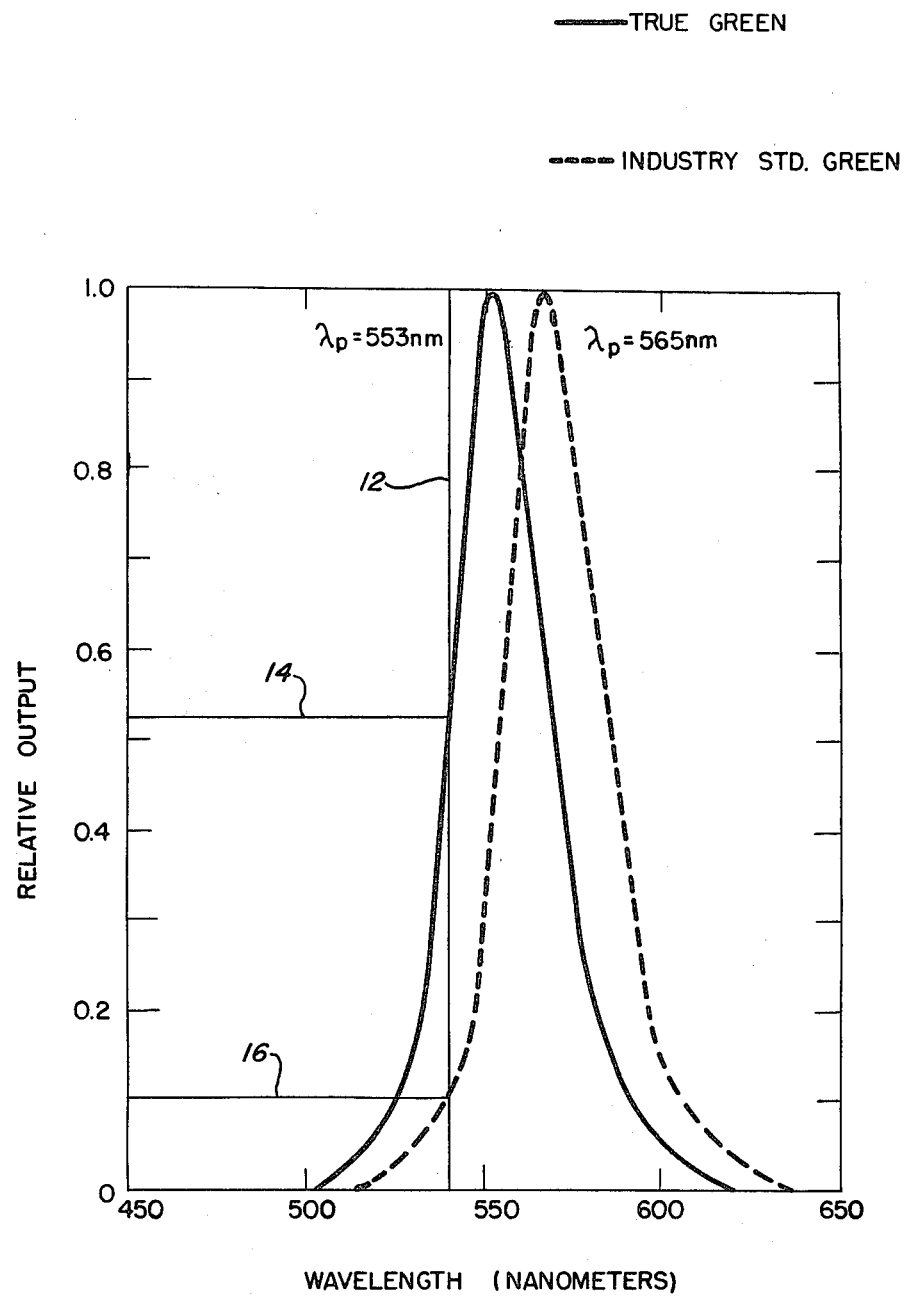
FIG. 2 is a graph of light output versus wavelength for two different light-emitting diodes.

The diode D1 is preferably an SPG-5401 green L.E.D. from Sorenson Lighted Controls Company, or its equivalent. This particular device comprises an aluminum-doped gallium phosphide (GaP) material which has a true green peak output wavelength. So-called "green" L.E.D.'s used in the past have been undoped GaP devices with peak output wavelengths considerably further into the yellow region, equipped with green lens packages to filter out some of the yellow component. In FIG. 2 the dashed line represents the unfiltered spectral output of such an undoped device, for example a General Instrument Company MV5274, which is seen to have a peak wavelength of about 565 nm., substantially more yellow than the 540 nm. wavelength of interest. The solid line graph, however, represents the unfiltered spectral output of the aluminum-doped device D1, which has an unfiltered peak output of about 553 nm., in the green region and much closer to 540 nm. The bandwidth of both devices is broad enough to encompass the 540 nm. region (vertical line 12), but the output of the doped material (solid line) is much greater at that wavelength than the output of the undoped material (dashed line). For purposes of a rough comparison, horizontal line 14 shows the relative output of the doped device while horizontal line 16 shows the relative output of the undoped device, each at 540 nm. There is at least a five-fold difference in relative output level at that wavelength.

Figure 3:
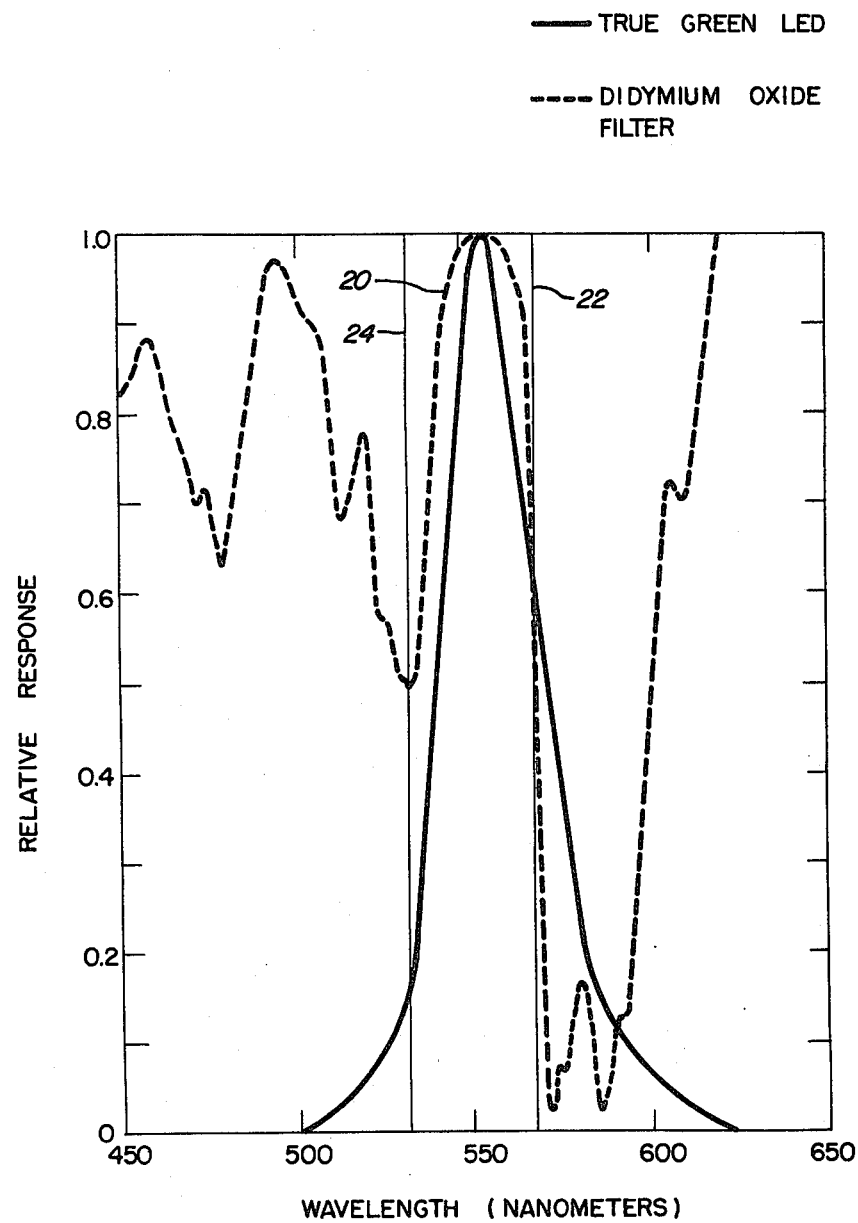
FIG. 3 is a graph of light output versus wavelength for one of these diodes, superimposed upon the transmission characteristic curve for a particular optical filter material.

The light output of the diode D1 is focussed by biconvex lenses L1 and L2 and passes through a filter F1. The filter serves to block out the longer wavelength, or yellow, portion of the light output of diode D1, as illustrated in FIG. 3. There the solid line again represents the spectral output of diode D1, and the dashed line represents the passband of the filter F1. The latter is preferably a 2 mm. thickness of didymium-oxide-doped glass, such as an S-8801 filter from Schott Optical Company. (Didymium is a mixture of the lanthanide or rare earth metals neodymium and praseodymium.) In the region of interest this material has a pass-band 20 with a long wavelength cut-off 22 at about 565 nm. and a short wavelength cut-off 24 which is somewhere below the short wavelength cut-off of the emission band of diode D1. As a result of the long wavelength cut-off 22, the already small amount of unwanted yellow illumination is further reduced, without blocking the peak emission in the green band surrounding 540 nm. If the green-yellow diode of FIG. 2 were used with this filter, most of its light output would be blocked, and the remaining output in the 540 nm. region (pass-band 20) would be respectively low.

Figure 4:
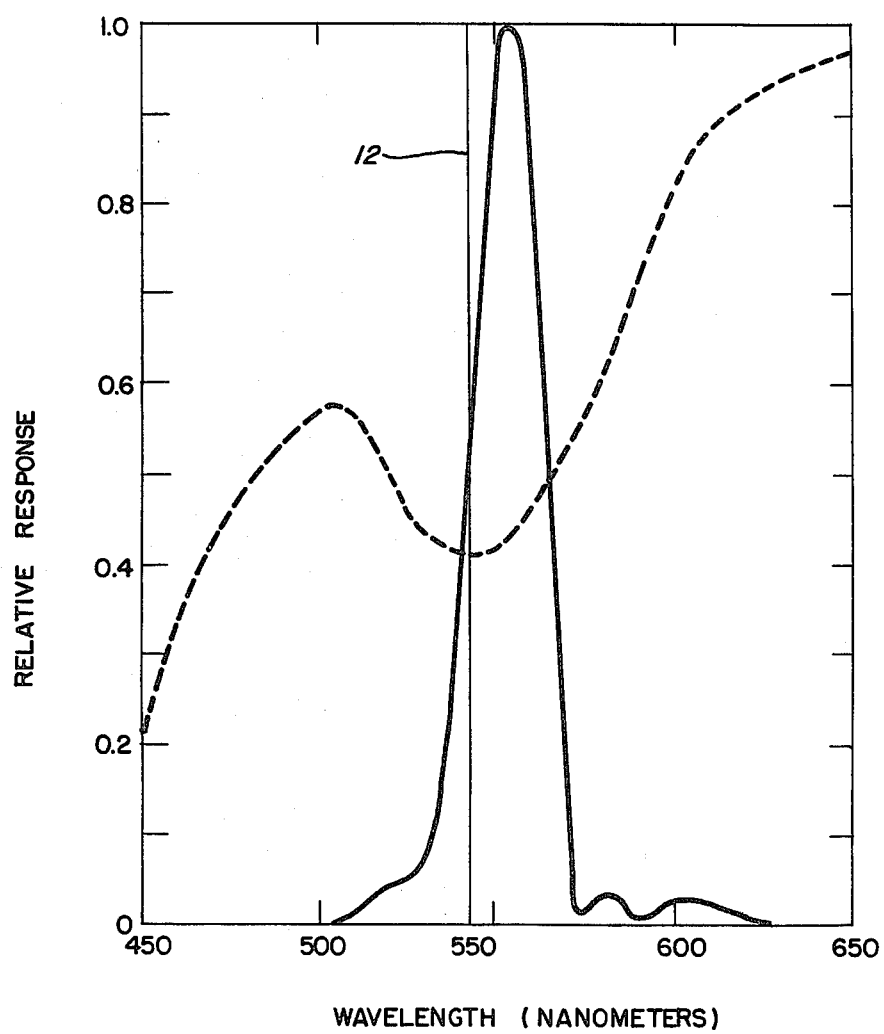
FIG. 4 is a graph of the light output of that diode after passage through that optical filter, superimposed upon a transmission curve for a sample of human blood prepared for analysis with this instrument.

The filtered output obtained by interposing filter F1 in front of diode D1 is illustrated by the solid line curve in FIG. 4. Approximately 85% of the radiant energy emerging from the filter is in the band from 520 to 565 nm., and the peak energy is at about 553 nm. The dashed line curve in FIG. 4 shows the spectral transmission characteristic of a sample of human blood prepared according to a standard method (the cyanmethemoglobin technique), and diluted 251:1 in a standard reagent (Drabkin's solution) so that the end concentration of hemoglobin is 14.6 gm./dl. This curve has a transmission minimum (absorption maximum) at the characteristic hemoglobin absorption wavelength of 540 nm. (line 12). Thus the hemoglobin absorption maximum and the illumination peak are as close together as possible, and the total wavelength spread is confined as narrowly as possible.

The lenses focus the light beam upon a sample chamber 18 (schematically illustrated) containing a properly prepared clinical sample of human blood. (The sample can also be mounted upon a slide.) As the light beam passes through the sample, a fraction of the 540 nm. component thereof is selectively absorbed by the hemoglobin content of the sample, this absorption being related to the hemoglobin concentration by Beer's Law. Thus, the emerging light beam has a reduced power level in the 540 nm. region, and the extent of the relative power reduction reveals the hemoglobin concentration of the sample, which is of clinical significance.

The light beam emerging from the sample impinges on a photodetector diode D2. The photodetector is preferably a blue-enhanced solid-state silicon photodiode such as Vactec Company's VTB-5041. Solid-state photodetection devices consume considerably less power than photomultipliers or other types of vacuum tube photocells.

The output of the photodector diode D2 is boosted by a pre-amplifier circuit A1, which is preferably a solid-state integrated circuit operational amplifier such as a CA3140AT from Radio Corporation of America. The light level transmitted by the sample is an inverse function of hemoglobin concentration. The cathode of the photodetector D2 is connected to the inverting input of the amplifier A1, so that the amplifier output is a positive voltage which decreases as the hemoglobin concentration becomes greater.

A logarithmic amplifier A2 provides logarithmic to linear conversion. This is necessary in order to obtain a linear output, because the light transmitted by the sample is logarithmically related to hemoglobin concentration. Amplifier A2 is preferably a solid-state integrated circuit device such as the 4127JG from Burr-Brown Co.

The output voltage of amplifier A2 is a logarithmically converted, amplified version of the output of the photodetector D2. Hence it is a linear, amplified analog signal representing hemoglobin concentration in the blood sample, within the limits of accuracy permitted by the spectral purity of the filtered radiation. This hemoglobin concentration signal is delivered to an analog-to-digital converter IC2, which is preferably a solid-state integrated circuit such as Intersil Co.'s ICL-7106 or the equivalent. The digitally converted output drives a reflective (e.g. liquid crystal) digital display L.C.D., which can be an FE0535-01 from Tempor, Inc. or its equivalent.

All the signal processing circuits A1, A2 and IC2 and the display L.C.D. are circuits of the type which minimize power consumption; i.e. they all are excusively solid-state devices, and in addition the display is the reflective type which does not produce its own light. Minimizing power consumption, even apart from the fact that it enhances accuracy by maximizing battery life and thus providing a more constant current supply, has a further advantage of considerable importance. The lower the current consumption is, the less heat is dissipated within the case enclosing the hemoglobinometer, and the lower is the operating temperature of the device. This materially assists in maintaining accuracy, because the performance of several components (notably R6, R7, R8 and D2) is measurably degraded by elevated temperature; and this source of inaccuracy cannot be economically eliminated. The analog/digital conversion accuracy of IC2 is also adversely affected by elevated temperature, because its internal reference voltage circuitry is temperature-sensitive.

In addition, signal processing circuits A1, A2 and IC2 all embody sophisticated designs which are essentially independent of power supply voltage down to threshold levels.

This hemoglobinometer can be used with either the oxyhemoglobin or the cyanmethemoglobin method. A switch S3 selects between two differently adjusted potentiometers R7 and R8 in order to determine the gain of amplifier A2. The gain so chosen determines the proper scale factor for the desired method; i.e. R7 for the oxyhemoglobin method and R8 for the cyanmethemoglobin method. Switch S3 also has a center "off" position. The oxyhemoglobin method involves the direct use of whole blood hemolyzed with saponin. In the cyanmethemoglobin method, ferricyanide is used to convert the iron in hemoglobin from the ferrous to the ferric state forming methemoglobin; and the latter combines with potassium cyanide to produce the stable pigment cyanmethemoglobin. Drabkin's solution is used as a combination reagent and diluent. R7 and R8 are factory-set. The difference in their settings reflects the difference in absorption coefficients, at 540 nm, between the oxyhemoglobin and cyanmethomoglobin preparations.

Switches S1 and S2 are ganged with S3, and all three are of the momentary type in order to further conserve power. When S3 is transferred to either side of its center "off" position, it automatically causes S1 and S2 to close at the same time, thus turning on the instrument for either an oxyhemoglobin or a cyanmethemoglobin determination. When S3 is later released, it returns to its center "off" position, and S1 and S2 also return to their "off" positions, terminating power usage.

Potentiometers R5 and R9 provide zero setting for the amplifiers A1 and A2 respectively. R5 is a dark current adjustment. It is factory-set and inaccessible to the user. R9, however, is accessible to the user and is routinely used for zero set during normal operation. Prior to sample measurement, a sample cell containing a control such as Drabkin's solution is employed, and R9 is adjusted until the L.C.D. display reads zero. Occasionally a calibration slide can be used to verify accuracy.

As an additional feature of this invention, the circuit described herein can also be used for blood turbidity testing by simply employing an infra-red source in place of the green light source D1. The methodology and clinical significance of blood turbidity testing are well known. According to "Reference Procedure for the Quantitative Determination of Hemoglobin in Blood" (National Committee for Clinical Laboratory Standards, Villanova, Pa., 1979), a hemoglobinometer reading may be falsely elevated because of light scattering caused by particulate matter, particularly blood lipoproteins, suspended in the clinical sample. The necessary correction in the hemoglobin reading may be made by measuring the same sample for turbidity alone, at a wavelength (e.g. the near infra-red) which is not absorbed by hemoglobin. Then the turbidity reading can be subtracted from the falsely elevated hemoglobin reading to obtain a corrected hemoglobin determination. If the turbidity is caused by elevated levels of blood lipoprotein, the infra-red turbidity reading also has clinical significance in itself as a diagnostic test for lipemia, i.e. excessive blood lipid levels, a condition which has been clinically correlated with cardiovascular disease.

In order to add these correctional and diagnostic capabilities to the instrument of this invention, an alternate illumination source D3, which can be any conventional infra-red L.E.D., is employed to illuminate the sample cell 18 when a switch S4 is operated to take the green diode D1 out of the circuit. The infra-red illumination from D3 is focussed by lenses L1 and L2, passes through the test sample, and impinges on the photodetector diode D2. (The didymium oxide filter F1 is essentially transparent to near infra-red, and so can be left in place.) The circuit gives a direct digital read-out of blood turbidity; and when used in this mode it has many of the advantages discussed above in connection with the hemoglobin determination.

It will now be appreciated that this hemoglobinometer is an inexpensive and convenient portable instrument which occupies a small volume, which is dedicated exclusively to blood testing by the oxyhemoglobin, cyanmethemoglobin and turbidity methods, and which achieves high accuracy by simultaneously minimizing all sources of error relating to constancy and spectral purity of the light source.

The described embodiments represent the preferred form of the invention, but alternative embodiments may be imagined which would come within the novel teachings herein. Accordingly, these embodiments are to be considered as merely illustrative, and not as limiting the scope of the following claims.

I claim:

1. A high accuracy portable hemoglobinometer comprising:
    means for deriving power from at least one portable power cell;
    solid-state means for regulating the current output of said power cell;
    solid-state light-emitting diode means having an unfiltered peak output wavelength not longer than about 553 nanometers connected to be powered by said regulated current output so as to be driven at constant brightness;
    filter means having a long-wavelength transmission cut-off of not more than about 565 nanometers interposed in the path of the light output of said light-emitting diode means;
    means interposed in said light output path and adapted to receive a blood sample;
    solid-state photodetector means positioned to measure the intensity of light from said light-emitting diode means transmitted through said sample;
    solid-state means arranged to logarithmically convert a light intensity measurement signal from said photodetector means;
    and reflective solid-state display means responsive to said logarithmic conversion means to display the quantitative result of said logarithmic conversion.

2. A hemoglobinometer as in claim 1 wherein said solid-state light-emitting diode is formed of aluminum-doped gallium phosphide.

3. A hemoglobinometer as in claim 1 wherein said filter means comprises a transparent body impregnated with didymium oxide.

4. A hemoglobinometer as in claim 1 further comprising:
    amplifying means having a plurality of alternative gaindetermining circuits operatively interposed between said photodetector means and said display means to determine the scale factor relating said light intensity measurement to the quantity displayed;
    and switching means for manually selecting one of said gaindetermining circuits;
    whereby to choose a scaling factor appropriate to one of a plurality of chemical systems for hemoglobin determination.

5. A dual purpose blood test instrument as in claim 1, further comprising:
    an infra-red radiation source in the form of a second solid-state light-emitting diode means directed to illuminate said sample;
    and means for connecting one or the other of said light-emitting diode means to said regulated current output.

6. A hemoglobinometer as in claim 1 further comprising:
    solid-state means for digital conversion of said logarithmically converted measurement;
    said display means being of the digital type and responsive to the output of said digital conversion means.

* * * * *